(12) United States Patent
Yamashita et al.

(10) Patent No.: US 9,464,266 B2
(45) Date of Patent: Oct. 11, 2016

(54) SENSOR UNIT AND CONSTANT-TEMPERATURE DEVICE

(75) Inventors: Seishi Yamashita, Fukuyama (JP); Tomonori Miwada, Fukuyama (JP)

(73) Assignee: RORZE CORPORATION (JP)

( * ) Notice: Subject to any disclaimer, the term of this patent is extended or adjusted under 35 U.S.C. 154(b) by 156 days.

(21) Appl. No.: 14/126,239

(22) PCT Filed: Jun. 11, 2012

(86) PCT No.: PCT/JP2012/064881
§ 371 (c)(1),
(2), (4) Date: Dec. 13, 2013

(87) PCT Pub. No.: WO2012/173076
PCT Pub. Date: Dec. 20, 2012

(65) Prior Publication Data
US 2014/0120610 A1    May 1, 2014

(30) Foreign Application Priority Data

Jun. 14, 2011  (JP) .................................. 2011-131825

(51) Int. Cl.
*C12M 1/00*    (2006.01)
*C12M 1/12*    (2006.01)

(52) U.S. Cl.
CPC ............. *C12M 41/14* (2013.01); *C12M 37/02* (2013.01)

(58) Field of Classification Search
CPC .............................. C12M 37/02; C12M 41/14
USPC ..................................................... 435/297.2
See application file for complete search history.

(56) References Cited

U.S. PATENT DOCUMENTS

| | | | |
|---|---|---|---|
| 4,868,122 A * | 9/1989 | Kominek ................ | B25J 21/02 |
| | | | 435/303.1 |
| 5,882,918 A * | 3/1999 | Goffe ......................... | 435/297.4 |
| 6,562,616 B1 * | 5/2003 | Toner et al. .............. | 435/297.2 |
| 2006/0057713 A1 * | 3/2006 | Cecchi ....................... | 435/303.1 |
| 2010/0120139 A1 * | 5/2010 | Busujima et al. ......... | 435/303.2 |

FOREIGN PATENT DOCUMENTS

| EP | 0967268 | * 12/1999 |
|---|---|---|
| JP | 2004-267064 | 9/2004 |
| JP | 2007-236216 | 9/2007 |
| JP | 2010-057376 | 3/2010 |
| JP | 2010-154792 | 7/2010 |

OTHER PUBLICATIONS

Machine translation EP 0967268 (Dec. 1999).*

* cited by examiner

*Primary Examiner* — Michael Hobbs
(74) *Attorney, Agent, or Firm* — Merek, Blackmon & Voorhees, LLC (57) ABSTRACT

In order to enable the inside of a constant-temperature device to be sterilized using sterilization gas and prevent contamination during incubation, even when provided with an atmosphere measuring means having a $CO^2$ sensor and an oxygen concentration sensor, a sensor unit (100) is arranged inside or close to an incubation chamber, and the internal atmosphere is measured by sucking-in the atmosphere of the incubation chamber (2) by means of an air-flow generation means (20). Furthermore, high-precision filters (23, 24) are arranged in the flow channel through which the atmosphere within the incubation chamber (2) is taken-in/discharged, preventing bacteria and/or cells from flowing in, and also preventing the diffusion of sterilization gas to the inside of a sensor unit (100) during sterilization.

16 Claims, 8 Drawing Sheets

SENSOR UNIT AND CONSTANT-TEMPERATURE DEVICE

FIELD OF THE INVENTION

The present invention relates to a device used to keep atmosphere inside an incubation chamber such as temperature, humidity, oxygen concentration and carbon dioxide concentration stable.

BACKGROUND OF THE INVENTION

An incubator is widely used as a device to keep and culture samples used for culturing and testing microbes or cells. The incubator has various instruments to maintain environmental condition such as temperature, humidity, oxygen concentration and carbon dioxide concentration in an incubation chamber in which the samples are stored. In culturing, the incubation chamber is maintained in high humidity state equal to or more than 90% of humidity at temperature 37° C. In order to maintain the specified culture environment, the incubator has atmosphere measuring means such as a temperature-humidity sensor, a carbon dioxide sensor, and an oxygen concentration sensor thereinside, and besides a control device to keep the inside in a specified environment from datum detected by the atmosphere measuring means.

When atmospheric unwanted bacteria, cultured cells or microbes remain in the incubation chamber, so-called contamination occurs in next culture because the unwanted bacteria and so on are mixed with a culture medium, therefore bringing bad influences to the cells and the microbes under culture. Accordingly, an operation called sterilization is required to remove bacteria other than the purpose before starting culture.

For the conventional incubator, is adopted a sterilization method to irradiate ultraviolet rays or a sterilization method called dry heat sterilization to kill the unwanted bacteria by keeping inside temperature equal to or more than 130° C. However, there are problems in these methods, for example, the sterilization is insufficient or it takes long time to start the next culture from the expiration of the sterilization. Therefore, gaseous sterilization, in which sterilizing is performed the incubation chamber by an impregnated sterilization gas such as hydrogen peroxide gas and ozone, has been recently widespread, and an incubator with a gaseous sterilization function has become common.

PRIOR ART

Patent Literature

Patent literature 1: Japanese Patent Laid Open Publication No. 2004-267064

DISCLOSURE OF THE INVENTION

Problems to be Solved by the Invention

The gaseous sterilization is a method for killing the unwanted bacteria by sterilizing power of sterilization gas flown into the incubation chamber, drastically shortening an interval from an end of culture to the next start of culture. It takes several hours until the temperature in the chamber returns to cultivable temperature from the start of heating in dry heat sterilization, however, according to hydrogen peroxide sterilization, for example, it can be finished in approximately one hour.

On the other hand, a malfunction often occurs in even incubators with gaseous sterilization function during the gaseous sterilization. Specially, an oxidized gas such as hydrogen peroxide or ozone corrodes detecting elements and metal parts of the atmosphere measuring means located in the incubation chamber and passages that communicate with the incubation chamber. Therefore, the atmosphere cannot be exactly detected in the incubation chamber during culturing. Further, since all assorts of atmosphere measuring means are expensive, cost increases if the atmosphere measuring means must be changed at every sterilizing operations.

Means to Solve the Problem

This invention was created to solve the above mentioned problems effectively.

A sensor unit as claimed in claim 1 is characterized in having a block having an interior space communicated with an incubation chamber, an air-flow generation means for sucking atmosphere from the incubation chamber to the interior space and discharging it into the incubation chamber, an atmosphere measuring means for measuring atmosphere in the interior space, a filter arranged between the incubation chamber and the interior space, and a heater for heating the atmosphere sucked through the filter.

Thus constructed sensor unit can be located in the inside or anywhere near the incubation chamber. Further, the pressure in the incubation chamber never decreases because the sucked atmosphere is returned by being discharged into the incubation chamber after being circulated. Although various pumps, axial fans, sirocco fans can be used as an air-flow generation means, it is preferable to use articles that a damp-proofed treatment is subjected in order to suck high-humidity atmosphere inside the incubation chamber. Further, it is preferable to use a filter made from moisture resistant material.

Effects of Invention

In using the sensor unit of the invention, the filter prevents the unwanted bacteria from entering the block in which an atmosphere measuring means such as a $CO_2$ sensor and an oxygen concentration sensor are located, thereby enabling to keep the atmosphere measuring means clean. Accordingly, the atmosphere measuring means does not need to be exposed to oxidizing strong gas such as hydrogen peroxide or ozone gas in order to give a sterilization treatment.

On the other hand, the filter separates the inside of the incubation chamber and the interior space of the block, and therefore, the air-flow generation means causes pressure difference through the filter. Accordingly, decompression suddenly occurs in the atmosphere sucked from the incubation chamber to the interior space of the block to lower the temperature. This temperature change causes dew condensation because the sucked atmosphere is under high humidity. However, in the invention, the interior space of the block is heated by the heater, thereby preventing the dew condensation from attaching on the atmosphere measuring means and affecting the humidity to be measured by the atmosphere measuring means.

PREFERRED EMBODIMENT OF THE INVENTION

Figure 1:
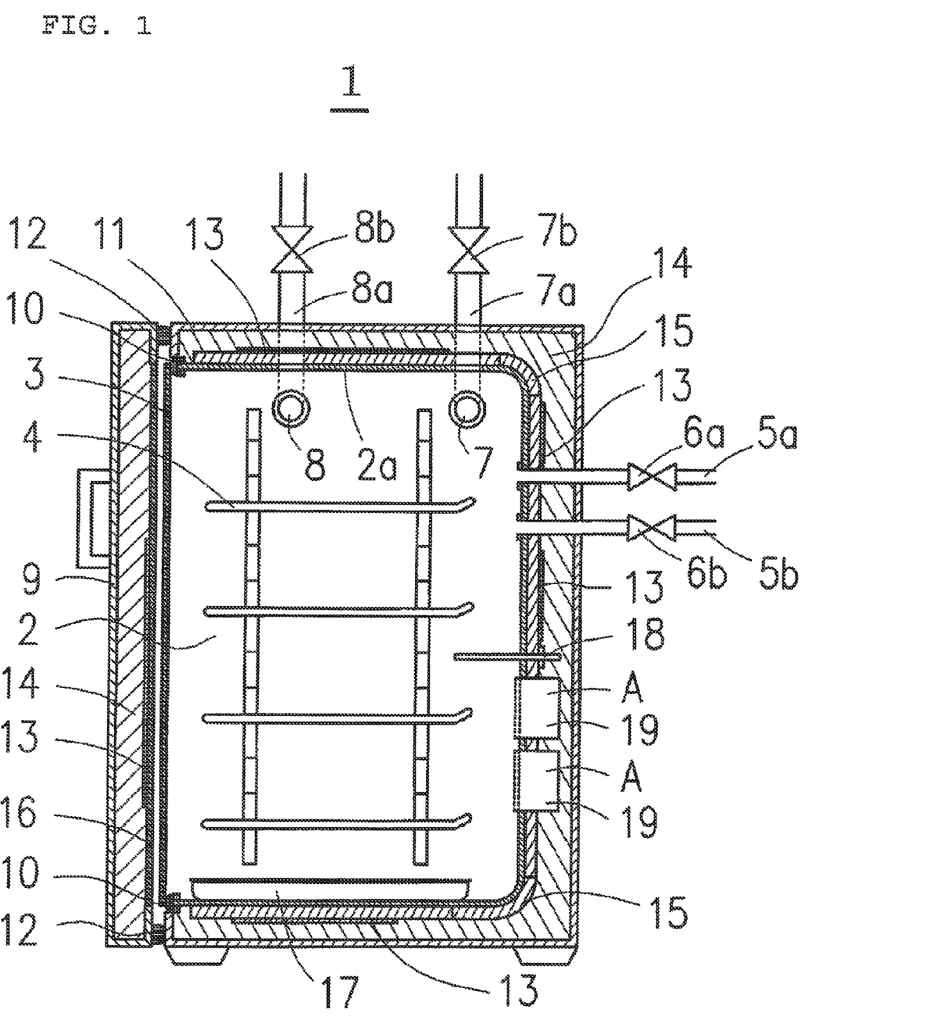
FIG. 1 is a sectional view of an incubator with a sensor unit.

The details of the invention will be explained with reference to illustrated embodiments below. FIG. 1 is a sectional view of an incubator 1 having a sensor unit 100, which shows an embodiment of the invention. The incubator 1 has an incubation chamber 2, an inner door 3, sample shelves 4 on which specimens are mounted, a supply pipe 5 for gas such as $CO_2$ and $N_2$ to be supplied into the incubation chamber 2 during culturing, an atmosphere measuring means 19, the sensor unit 100 for sucking and discharging internal atmosphere, a supply port 7 for supplying gas for sterilization such as hydrogen peroxide and ozone, and a suction port 8 for drawing the supplied gas. The incubation chamber 2 is a rectangular parallelepiped having an opening to the front face and formed from a wall 2a consisting of materials superior in thermal conductivity and corrosion resistance such as aluminum and stainless steel, and an inner door 3 installed to the opening of the wall 2a through a hinge so as to open and close. The inner door 3 is so constructed that the inside of the incubation chamber 2 is airtight when the opening of the incubation chamber 2 is closed through a packing 10.

An outer case 11 having an opening to the front face is arranged to the outside of the wall 2a of the incubation chamber 2 so as to accommodate the incubation chamber 2. The outer case 11 is made from a sheet metal such as iron material by folding or pressing, and the opening of the outer case 11 is turned to the same direction as the opening of the incubation chamber 2. A peripheral edge of the opening of the outer case 11 is bent toward the incubation chamber 2. An outer door 9 is provided to the opening of the outer case 11 through a hinge so as to open and close. The outer door 9 is so constructed that the inside of the outer case 11 is airtight when the opening of the outer case 11 is closed through a packing 12.

A metallic board having high thermal conductivity such as copper or aluminum is closely fixed to the wall 2a of the incubation chamber 2, and further electric heaters 13 are directly and closely fixed on the outside of the wall 2a. Besides, a heat insulator material 14 is provided so as to surround all members mounted on the wall 2a. The wall 2a of the incubation chamber 2 is directly heated with the electric heaters 13, thereby controlling the inside of the incubation chamber 2 to the predetermined temperature. A soaking board 15 made of metal having a high thermal conductivity such as copper or aluminum is located on the outer wall surface of the incubation chamber 2, and the wall surface of the incubation chamber 2 is heated through the soaking board 15. According to this, even each electric heater 13 having a small area can heat the whole of wall 2a of the incubation chamber 2 uniformly. Further, although this embodiment adopts a so-called direct heat method for directly heating the wall 2a with the electric heaters 13, an air jacket method or a water jacket method for heating the inside by placing a tube for circulating heated air on the wall 2a can be also adopted.

The outer door 9 of box shape is formed from the members similar to the outer case 11, having an inner panel 16 made of aluminum mounted on the side facing the opening of the incubation chamber 2. The outer case 11 has a heat insulator 14 provided to the inside to prevent heat of an electric heater 13 placed on the inner panel 16 of the outer case 11 side from leaking from the outer door 9 to the outside. A packing 12 is provided to the peripheral edge of the outer door 9 facing the opening portion of the outer case 11. When closing the outer door 9, the packing 12 seals the opening portion by contacting to a flanged-shaped bent portion which is formed to the peripheral of the opening of the outer case 11.

A plurality of sample shelves 4 for placing samples to be used in culture and test are located in the incubation chamber 2 at predetermined intervals in the vertical direction. A water tray 17 into which distilled water is poured to humidify the inside of the incubation chamber 2 is placed on the floor of the incubation chamber 2, thereby enabling to keep the inside of the incubation chamber 2 at the predetermined temperature by being heated with an electric heater 13 provided outside of the floor of the incubation chamber 2.

The incubation chamber 2 has a $CO_2$ supply pipe 5a with a purity equal to or more than 99% and a $N_2$ supply pipe 5b with a purity equal to or more than 99% from the outside, and these gases are supplied from not illustrated gas supply means into the incubation chamber 2 through each of the pipes 5a, 5b. The pipes 5a, 5b respectively have electromagnetically driven switching valves 6a, 6b to regulate switching operation by inputting signal from a not illustrated incubator control means. Besides, the gas supply means can have generators for various gases apart from the incubator 1 or them into the incubator 1. Further, cylinders can be filled with the various gases and located outside the incubator 1.

Besides, the incubation chamber 2 has a supply port 7 for supplying hydrogen peroxide gas, which is conveyed from a not illustrated hydrogen peroxide generator, into the incubation chamber 2 and a suction opening 8 for discharging air inside the incubation chamber 2 to the outside in sterilizing. The supply port 7 and the suction port 8 are communicated to the not illustrated hydrogen peroxide generator through a pipe 7a and a pipe 8a, respectively. And, electromagnetically driven switching valves 7b, 8b are provided to the pipes 7a, 7b, respectively. The switching valves 7b, 8b have opening and closing operations regulated by signals which are inputted from the not illustrated incubator control means. Besides, the supply port 7 supplies hydrogen peroxide gas into the incubation chamber 2 during sterilization. However, after the sterilization, the supply port 7 can supply clean air whose impurities are filtered with a highly-functional film to discharge the hydrogen peroxide gas which is collected in the incubation chamber 2 earlier.

Further, a thermal sensor 18 containing thermocouples and a resistance thermometer bulb is located to the incubation chamber 2, and the incubator control means controls a temperature inside the incubation chamber 2 to a desired value by regulating outputs of the electric heaters 13 with based on the electrical signals from the thermal sensor 18. The thermal sensor 18 has a temperature detecting portion kept in airtight with a metal protection pipe which is called a sheath made of stainless steel, and survives through extensive use in a high temperature and in a gas atmosphere. Besides, a thermocouple for measuring temperature is provided to the electric heaters 13 located around the wall 2a of the incubation chamber 2 individually, and an incubator control unit performs temperature control of each electric heater 13 individually. According to this, it is possible to reduce temperature unevenness and to make a uniform temperature environment. Further, it is possible to raise the temperature in the inside of the incubation chamber 2 in a short time, for example, by setting a temperature of the electric heater 13 for heating the water tray 17 higher than the surrounding electric heaters 13. Besides, it is possible to install a fun for stirring air inside the incubation chamber 2 in order to equalize an environment inside the incubation chamber 2. However, in this case, it is desirable to protect electrical parts inside the fun from hydrogen peroxide gas by putting a seal on moving parts of the fun in consideration of the sterilization by hydrogen peroxide gas.

Further, the incubator 1 has a $CO_2$ sensor and an oxygen sensor as an atmosphere measuring means 19 for measuring atmosphere such as temperature, humidity, $CO_2$ concentration and oxygen concentration inside the incubation chamber 2. The $CO_2$ sensor and the oxygen sensor are electrically connected to the incubator control unit, and the incubator control unit controls the environment inside the incubator chamber 2 to the predetermined $CO_2$ concentration and the oxygen concentration by controlling the operation of the valve 6a of the $CO_2$ supply pipe 5a based on the electrical signals from the $CO_2$ sensor and the operation of the valve 6b of the $N_2$ supply pipe 5b based on the electrical signals from the oxygen sensor. Besides, $N_2$ gas is used to control the oxygen concentration inside the incubation chamber 2 because Nitrogen is stable inert gas which accounts for 70% of the air and enables to keep the inside of the incubation chamber 2 in a low level of oxygen. Although the $CO_2$ sensor and the oxygen sensor are used as an atmosphere measuring means 19 in this embodiment, the $N_2$ supply pipe 5b, the valve 6b and the oxygen sensor are not required in case of the culture under low oxygen conditions.

Here, the atmosphere measuring means 19 such as the $CO_2$ sensor and the oxygen sensor have the detecting portion located in the incubation chamber 2 to measure the atmosphere inside the incubation chamber 2 with detecting elements. However, when these detecting elements, electronic components and wirings are exposed to the hydrogen peroxide gas atmosphere or the high humidity atmosphere for a long time, oxidation or corrosion interrupts an accurate measure. In the worst case, the culture is canceled.

Figure 2:
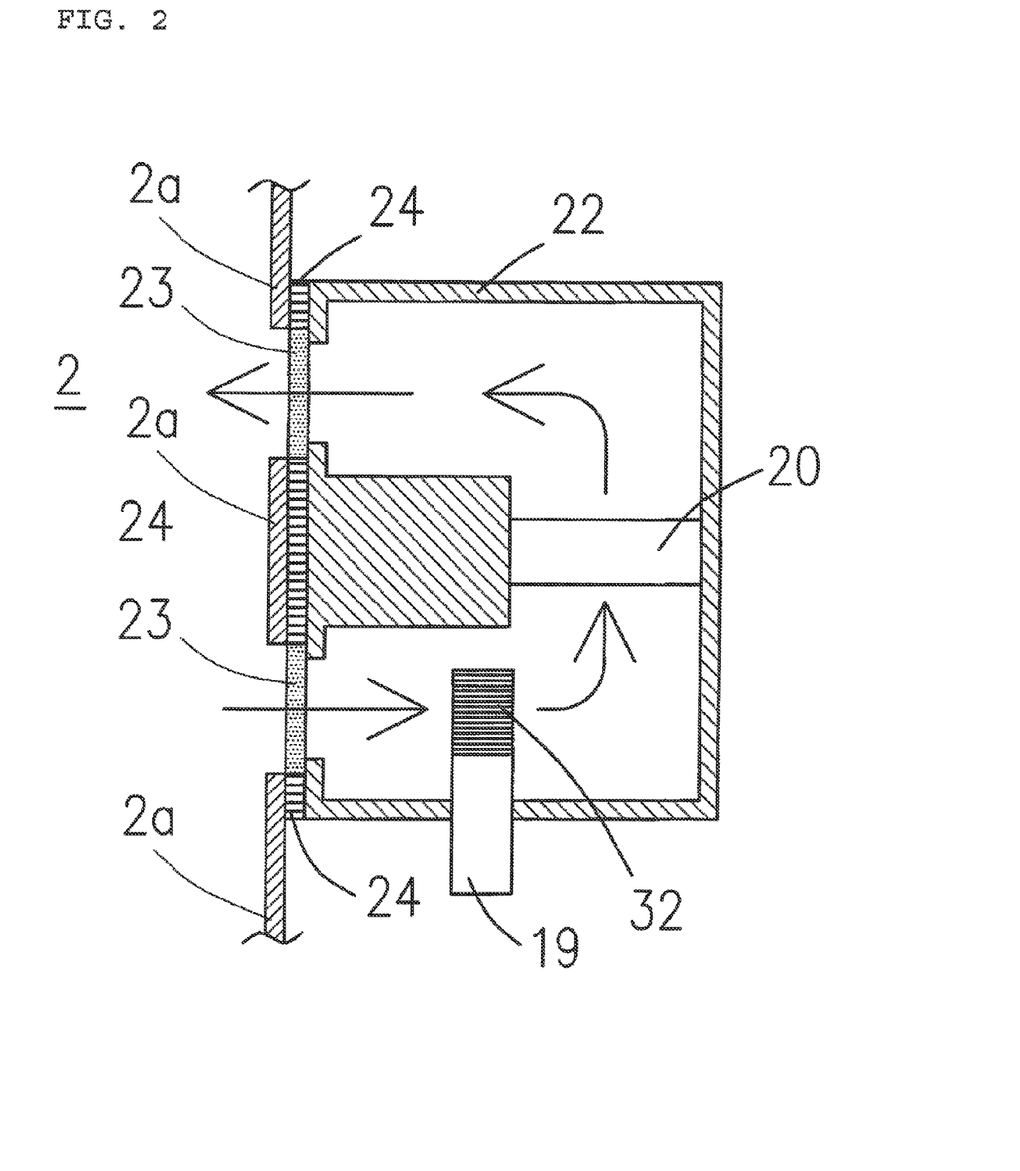
FIG. 2 is a pattern diagram of the sensor unit.

In the present invention, an interior space is formed in a block that is formed separately from the incubation chamber 2, and the atmosphere measuring means 19 and the air-flow generation means 20 are located therein. The atmosphere inside the incubation chamber 2 is measured by generating an air current with an air-flow generation means 20 so as to suck and discharge the air inside the incubation chamber 2 and arranging a detecting element 32 of the atmosphere measuring means 19 in a passage of the air current. Besides, the incubation chamber 2 is communicated to the interior space at an opening portion of the wall 2a of the incubation chamber 2 through the filter 23 (see FIG. 2). The present embodiment will be explained below in detail.

Figure 3:
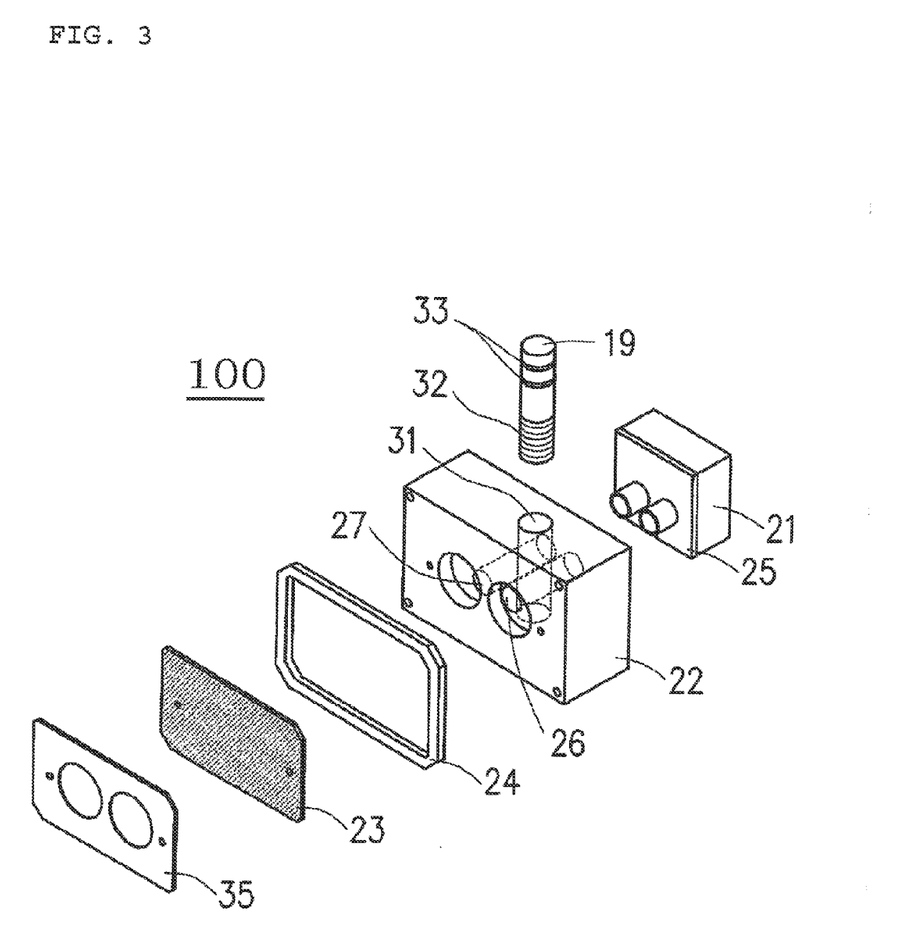
FIG. 3 is an exploded view showing a first embodiment of the sensor unit.
Figure 4:
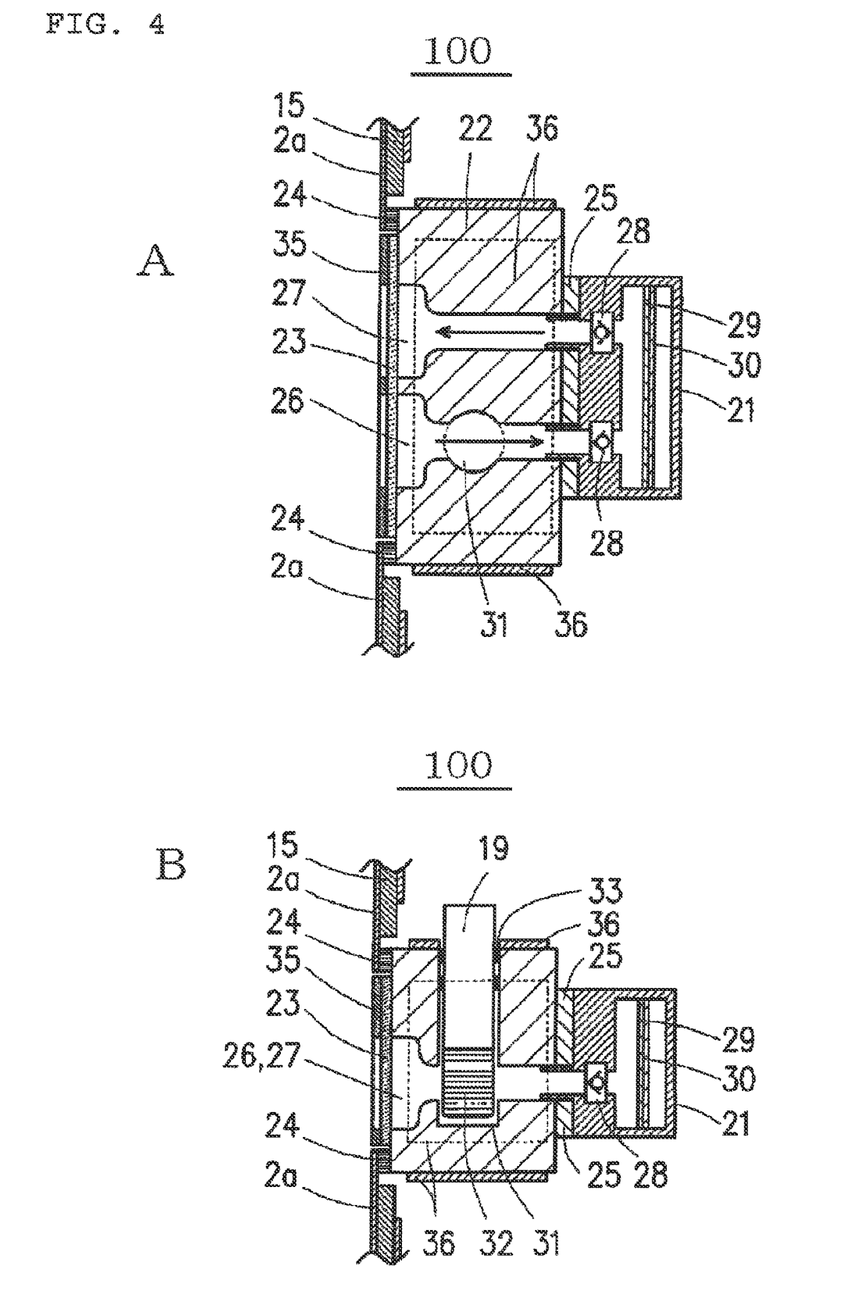
FIG. 4 is a sectional view showing the first embodiment of the sensor unit.

FIG. 3 is an exploded view showing each of members constructing one example of the sensor unit 100 of the present embodiment. FIG. 4A is a cross section viewed from the top face, and FIG. 4B is a cross section viewed from the side face. A body module 22, which is one of the component members of the sensor unit 100, is made in an aluminum block having a high thermal conductivity, whose surface has been subjected to Alumite treatment. The body module 22 has a smooth processed face contacting on the wall 2a of the incubation chamber 2, and a packing 24 is located between the smooth processed surface and the wall 2a. The packing 24 is larger than the periphery of the opening of the wall 2a of the incubation chamber 2, thereby bringing the body module 22 and the wall 2a into contact airtight.

The body module 22 has two thorough holes in a parallel relationship, which pierce from one surface to the other surface respectively. Here, the one surface is contacted on the wall 2a of the incubation chamber 2, and the two through holes are provided in a range partitioned off from the outside through the packing 24. The two through holes respectively correspond to an inhalation passage 26 and a discharge passage 27. A pump 21 of an air-flow generation means 20 is air-tightly fixed on a surface opposite to the surfaces of the inhalation passage 26 and the discharge passage 27 opposed to the wall 2a of the incubation chamber 2 (the other face of the body module 22). Besides, the pump 21 has a suction port and an exhaust port on one surface of the main body of the pump 21, and two through holes 26, 27 are formed to the positions corresponding to the suction port and the exhaust port. The through hole 26 communicates with the suction port of the pump 21, forming the passage 26 for inhaling the air from the incubation chamber 2 to the pump 21 by operating the pump 21. The through hole 27 communicates with the exhaust port of the pump 21, forming the passage 27 for discharging the air inhaled to the inside of the pump 21 into the incubation chamber 2 by operating the pump 21. Further, the pump 21 has a check valve 28 to each of the suction port and the exhaust port, thereby preventing the inhaled and discharged fluid from flowing in an opposite direction. According to the above mentioned structure, a current of air along one direction is formed to two flow channels of the inhalation passage 26 and the discharge passage 27 which are formed to the body module 22 so as to inhale the air inside the incubation chamber 2 and discharge into the incubation chamber 2 with the air generating means 20 (pump 21).

The pump 21 has a barrier 29 to partition a space inside the main body of the pump 21, having the outside air inhaled and discharged as changing the inside volume by expanding and reducing the barrier 29. Here, the pump 21 has a bimorph vibrator 30 as a means for expanding and reducing the barrier 29. The bimorph vibrator 30 is attached to the barrier 29 and driving pressure is applied thereon, thereby bending and stretching the bimorph vibrator 30 and the barrier 29 at a constant frequency. The bending and stretching operations change the volume inside the pump 21 to generate an air-flow. Besides, a pump such as a diaphragm-plunger pump for stretching a diaphragm that works as the barrier 29 by rotations of a motor, and a fan such as an axial fan or a sirocco fan can be also used as a means for generating the air-flow flowing through the inhalation passage 26 and the discharge passage 27 as well as the above. However, the air-flow flowing through the inhalation passage 26 and the discharge passage 27 becomes high humidity equal to or more than 90% of humidity, and therefore, it is preferable to choose an available article in the high humidity environment. Accordingly, the sensor unit 100 can inhale and discharge the air inside the incubation chamber 2 without mixing with the outside air.

Further, the body module 22 has a sensor hole 31 to insert the atmosphere measuring means 19 formed to be at right angles to the inhalation passage 26. The sensor hole 31 has shape and size suitable for the atmosphere measuring means 19, and a detecting portion 32 of the atmosphere measuring means 19 is formed so as to project toward the inhalation passage 26. Furthermore, it is desirable that members for sealing such as a packing and an O-ring are located into the gap between the atmosphere measuring means 19 and the sensor hole 31 in order to prevent the air communicating through the inhalation passage 26 from flowing out from the sensor unit 100 to the outside or the outside air from flowing into the inhalation passage 26.

The atmosphere measuring means 19 is provided between the inhalation passage 26 and the pump 21 in order to measure near the incubation chamber 2.

Further, in the sensor unit 100 of the present embodiment, a filter 23 is closely attached on a face abutting against the wall 2a through a presser plate 35 so as to cover the inhalation passage 26 and the discharge passage 27. Although the filter 23 is used by cutting what minute fibers made from stainless steel 316 is processed and sintered to appropriate dimensions, it may be formed from synthetic fibers such as polypropylene, polyester or polyolefin as well as the sintered metals. Besides, because the filter 23 has a filtration accuracy of approximately 1 μm, most unwanted bacteria, mold and cells causing contamination cannot flow into the sensor unit 100 passing through the filter 23. Therefore, even if the inside of the incubation chamber 2 is contaminated, the air inside the incubation chamber 2, which is inhaled into the sensor unit 100 with the pump 21, is kept in a high clean state where is filtrated by the filter 23. Further, because molecules such as $CO_2$, oxygen and water vapor can flow through the filter 23 having the filtration accuracy of 1 μm, the atmosphere inside the incubation chamber 2 can be precisely detected. Besides, although an even filter 23 having the filtration accuracy equal to or less than 0.1 μm can be used, it is necessary to examine performance about discharge pressure and the flow quantity of the air-flow generation means 20 such as a pump and a fun because the filter has high pressure loss in itself, in order to secure the detectable flow quantity of various sensors.

In addition to the above mentioned structure, the sensor unit 100 has a heater 36 (an electrical heater) for heating the body module 22. When the air having the humidity equal to or more than 90% inside the incubation chamber 2 is inhaled into the sensor unit 100, the pressure of the atmosphere inhaled through the filter is reduced to lower the temperature according to the pressure loss of the filter in itself. Therefore, the electrical heater 36 is provided to prevent dew condensation in the sensor unit 100, expressly near the inhalation passage 26 of a filter exit. For this purpose, it is essential to handle the pressure decrease by providing with the electrical heater 36 because the inside space of the block from the filter 23 of the inhalation passage 26 side to the air-flow generation means 20 (pump 21) becomes negative pressure than the inside of the incubation chamber 2.

When the air inhaled from the incubation chamber 2 is dew-condensed in the sensor unit 100, the sensor detecting element 32 is adversely affected to interfere exact detections. Besides, water vapor content in the air is decreased by the dew condensation to reduce the humidity in the incubation chamber 2. In the embodiment, the electric heater 36 is attached on the body module 22, thereby heating the whole body module 22 made of aluminum metal having high thermal conductivity. Because the incubation chamber is controlled to 37° C., the electric heater 36 continues regularly heating with amperage so that the inhaled air should not be dew-condensed. Therefore, special control is not needed. Further, the temperature can be controlled by providing with a thermocouple (not illustrated) for measuring the temperatures of the electric heater 36 and the body module 22.

On the other hand, the electric heater 36 is attached on the body module 22 so that the body module 22 is wholly heated, and therefore, a space from the air-flow generation means 20 (pump 21) to the discharge passage 27 is to be also heated. If it is to respond the pressure decrease, around the filter exit inside the sensor unit 100 should be particularly heated. However, heating not the portion but the body module 22 whole is to respond the dew condensation caused by temperature decrease that is exclusively caused by heat dissipation from the body module 22.

Besides, if it is so constructed that the dew concentration caused by the temperature decrease of the filter 23 at the inhalation passage 26 side is canceled by heating with the heater and besides the temperature to the discharge passage 27 is prevented from decreasing, the atmosphere measuring means 19 may be provided either between the inhalation passage 26 and the pump 21 or between the pump 21 and the discharge passage 27.

The electric heater 36 and the thermocouple are electrically connected to a incubator control unit to control the sensor unit 100 to the predetermined temperature. Here, if the sensor unit 100 is controlled in such a temperature that the air inhaled from the incubator chamber 2 should not be dew-condensed, it is possible to exactly measure the atmosphere inside the incubation chamber 2. Besides, it is possible to prevent the dew condensation of the filter 23 with the electric heater 36. When the filter 23 is dew-condensed, the dew-condensed water becomes an obstacle to prevent air of a sufficient amount from inhaling into the sensor unit 100. Consequently, an exact detection cannot be carried out. Further, the whole sensor unit 100 is enveloped by a thermal insulator (not illustrated).

The sensor unit 100 is fixed to the wall 2a of the incubation chamber 2. A fixing method can be applied for a method by providing tapped holes to the sensor unit 100 and fixing with screws from the inside of the incubation chamber 2 or by welding studs or nuts on the wall 2a of the incubation chamber 2 and fixing with the screws or the nuts from the outside of the incubation chamber 2. However, in considering shelter density of the incubation chamber 2, it is preferable that the sensor unit 100 is fixed from the outside by welding the studs or the nuts on the wall 2a of the incubation chamber 2 without forming through holes on the wall 2a. Besides, as for a method for fixing a filter 34 and a presser plate 35 on the body module 22, screwing is preferable in consideration of exchanging. In this case, it is desirable to use hexagonal screws that having no cross recesses or hexagon sockets on heads of the screws. Further, although there is no limitation where of the wall 2a the sensor unit 100 is installed, it is desirable to determine an appropriate detection position by measuring the specific gravity of gas and an air-flow state in the incubation chamber 2.

According to this embodiment, unwanted bacteria and spores floating in the incubation chamber 2, which cause a contamination, are prevented from flowing into the sensor unit 100 by the filter 23, and therefore, the cleanliness in the sensor unit 100 is always maintained. Besides, the unwanted bacteria and the spores that are prevented from flowing into the sensor unit 23 are killed by the sterilization gas such as hydrogen peroxide, so that a contamination is not caused in the next culture. Further, in case there is a possibility that the killed unwanted bacteria might become a hotbed of new unwanted bacteria, there becomes no possibility that the unwanted bacteria propagates if the filter 23 is changed for a new one at the time of sterilization. Furthermore, if the pump 21 stops inhaling the air inside the incubation chamber 2 during the sterilization, the sterilization gas rarely invades into the sensor unit 100.

Besides, the air that has been once inhaled from the incubation chamber 2 for a measurement passes through the passage inside the sensor unit 100, and thereafter, returns into the original incubation chamber 2, which is a common feature in another embodiment. It becomes easy to keep the atmosphere in the incubation chamber 2 stable because the pressure inside the incubation chamber 2 ceases to be reduced by returning the inhaled air into the incubation chamber 2.

It is possible to prevent most of the sterilization gas from communicating among the incubation chamber 2, the inhalation passage 26 and the discharge passage 27 by partitioning through the filter 23 as the above-mentioned first embodiment. However, the sterilizing gas molecules are diffused in the incubation chamber 2, and therefore, there is a possibility that the sterilizing gas molecules pass through the filter 23 and attach on the detecting portion of the sensor 19 (atmosphere measuring means). On the other hand, in a sensor unit 200 in the second embodiment, a check valve 28a is provided between the sensor 19 of the sensor unit 100 and the filter 23 to prevent the diffused molecules from flowing into the inhalation passage 26 (see FIG. 5). The check valve 28a is arranged between the filter 23 and a sensor hole 31, in which the sensor 19 of the inhalation passage 26 is provided, so as to pass the air-flow to be inhaled from the incubation chamber 2 into the inhalation passage 26 but stop the air-flow to be discharged from the incubation chamber 2 to the inhalation passage 26.

Figure 5:
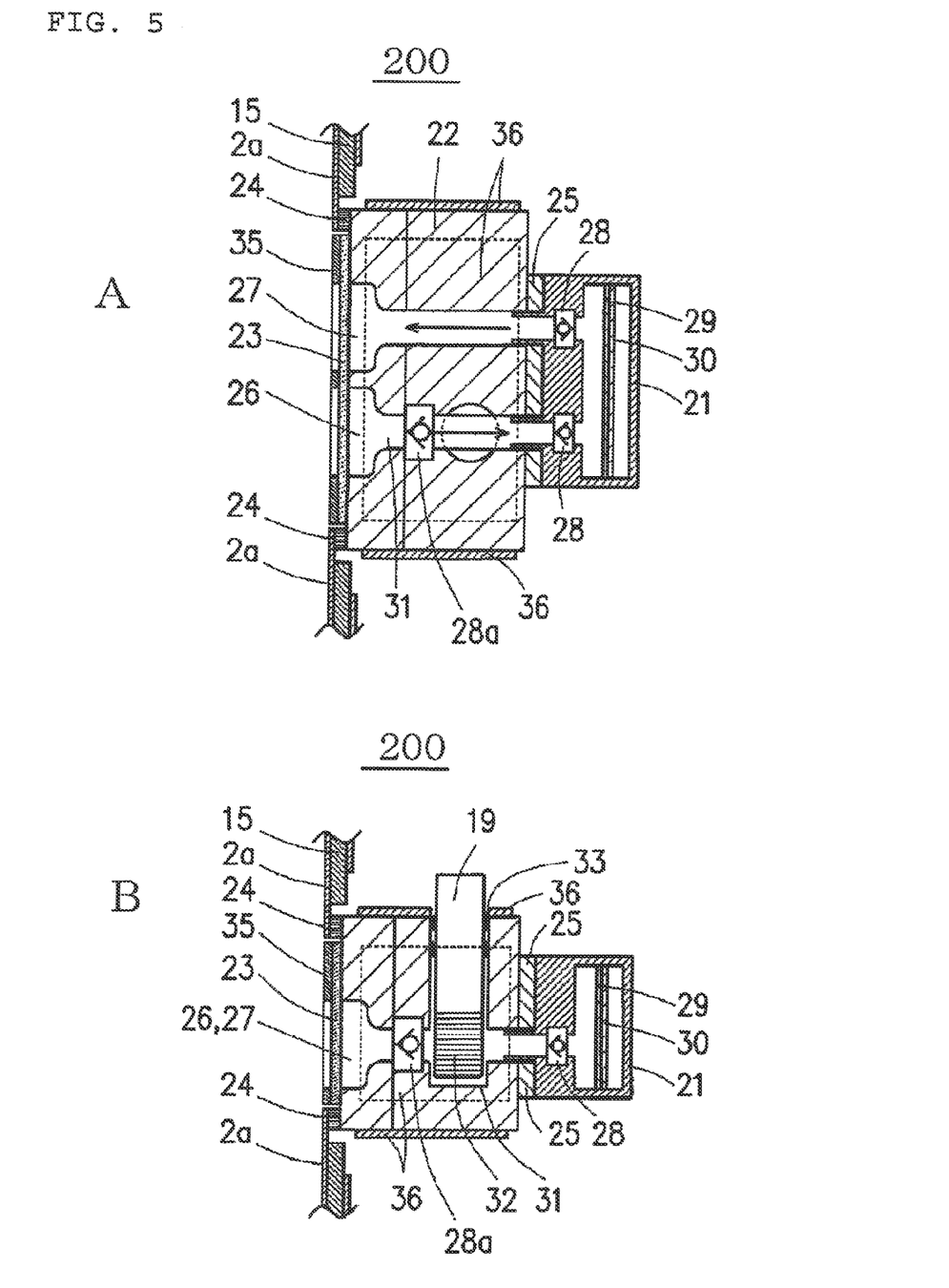
FIG. 5 is a sectional view showing a second embodiment of the sensor unit.

Here, the check valve 28a sets a threshold value that the valve does not pass a fluid if the passing fluid does not become equal to or more than the predetermined pressure even if the fluid is direct flow, which is called cracking pressure. When locating the check valve 28a having the cracking pressure that is equal to or more than the pressure of the sterilization gas owing to diffusion and equal to or less than the pressure inhalable for the pump 21, the air inside the incubation chamber 2 is inhaled and the sterilization gas is prevented from entering the sensor unit 200 by diffusion. Besides, when the check valve 28a is located between the filter 23 and the sensor hole 31, the check valve 28 of the inhalation passage 26 side, which is provided inside the pump 21 of the sensor unit 100, becomes unnecessary. Besides, the sterilization gas entering from the through hole 27 by molecular diffusion is prevented from entering by the check valve 28 provided to the discharge passage 27 side of the pump 21, thereby never reaching the detecting portion of the sensor 19.

Further, as for the sensor unit 200 of the present embodiment, a relief pressure valve or a safety valve can be installed in spite of the check valve 28a. In short, considering differences between the pressure of gas to be inhaled by the pump 21 and the pressure of the sterilization gas to be intruded by diffusion, the pump 21 should set the pressure so that the pressure of gas to be inhaled by the pump 21 become high and a valve opened by the pressure that is lower than the gaseous pressure inhaled with a pump 21 without being opened by the pressure by the diffusion of the sterilization gas should be located. However, when using a valve except for the check valve 28a, it is necessary to provide the check valve 28 to the inhalation passage 26 side of the pump 21.

Figure 6:
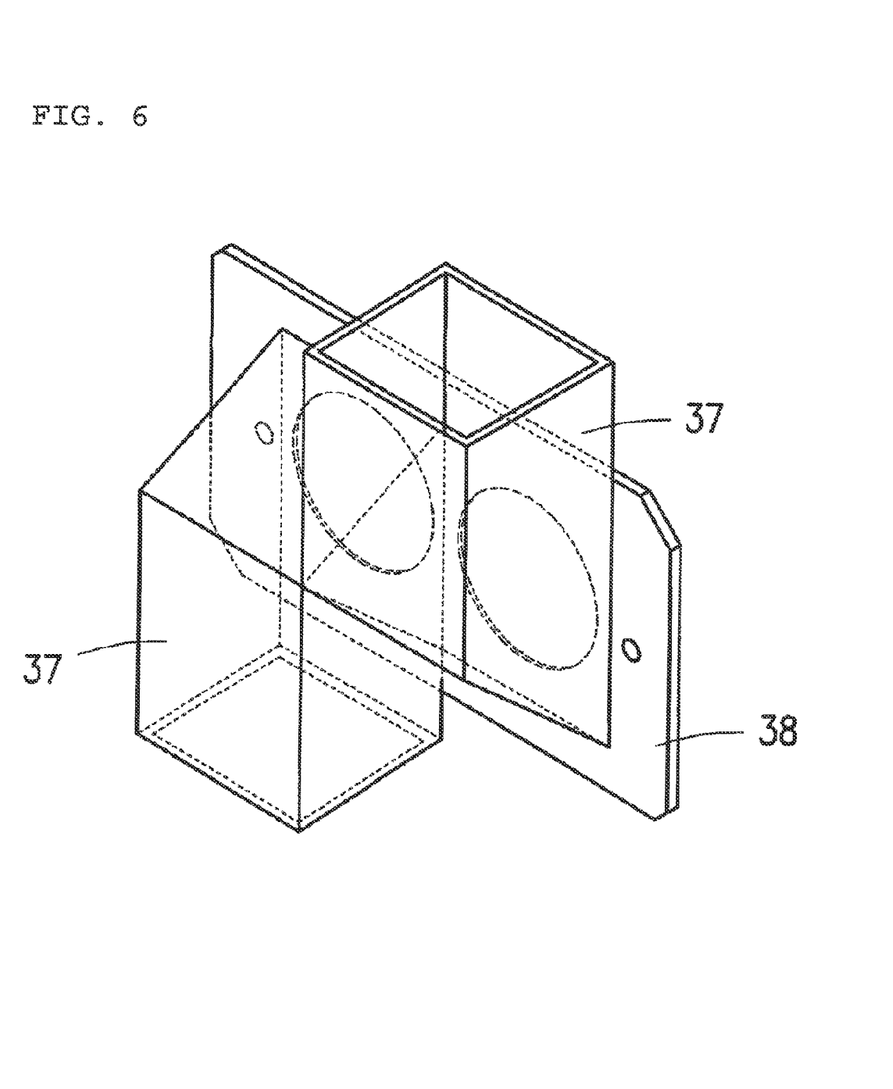
FIG. 6 is a view showing a duct with the sensor unit.

Besides, in the above-mentioned embodiment, the inhalation passage 26 and the discharge passage 27 are located so as to be mutually adjacent. This placement rarely causes a phenomenon that the air discharged from the discharge passage 27 is directly inhaled from the inhalation passage 26 without circulating inside the incubation chamber 2. When this phenomenon occurs, only an atmosphere of part of the incubation chamber 2 is continuously measured, and therefore, an atmosphere of the whole incubation chamber 2 would not be measured exactly. Then, it is possible to prevent the discharged air from being inhaled without change by mounting a presser plate 38 with a duct 37 to regulate the air-flows for inhaling and discharging on the sensor unit 100 of the above-mentioned embodiment (see FIG. 6). The duct 37 regulates the air-flows for inhaling and discharging, and the discharged air is diffused extensively inside the incubation chamber 2 without being directly inhaled. The duct 37 can control comfortable inhalation and discharge directions by being made rotatable.

Figure 7:
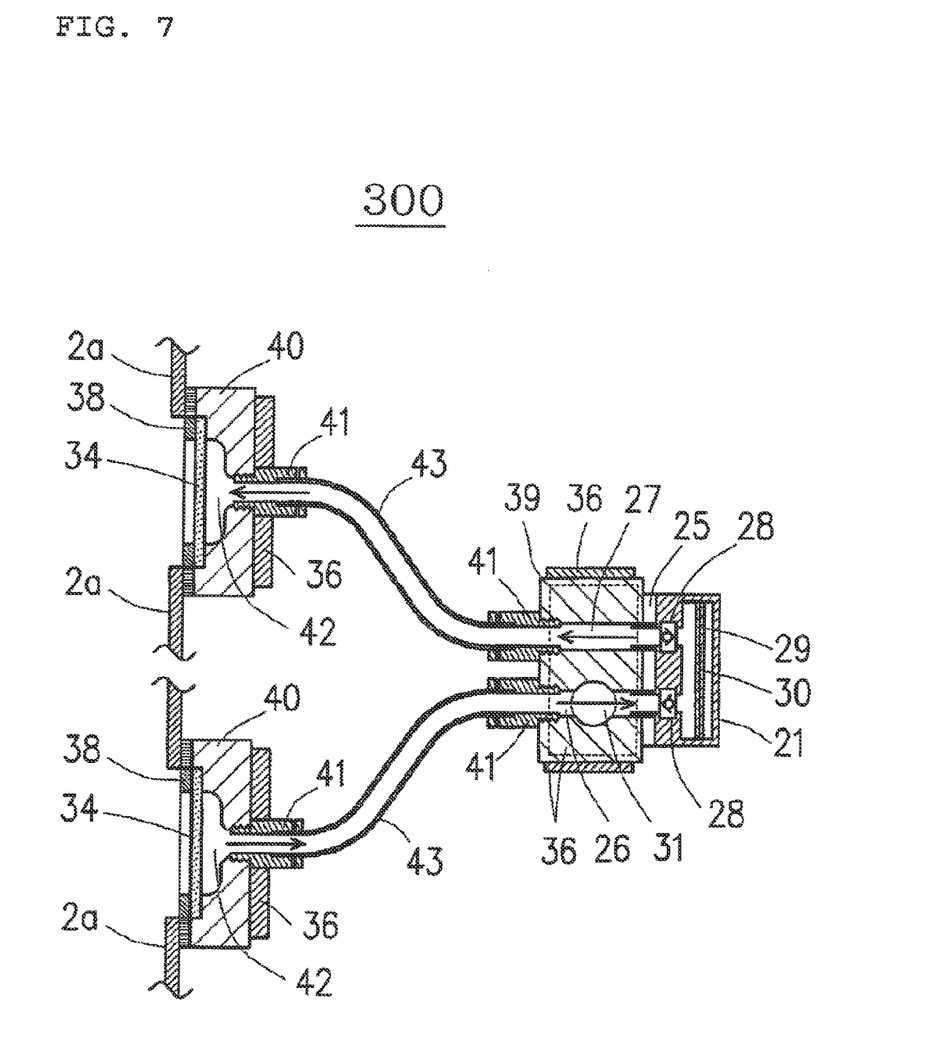
FIG. 7 is a sectional view showing the third embodiment of the sensor unit.

The above-mentioned first and second embodiments disclose the sensor units 100 and 200 having the inhalation passage 26 and the discharge passage 27 formed on the body module 22, respectively. Next, the third embodiment wherein the suction port to inhale air and the exhaust port to discharge air are individually arranged will be explained below. FIG. 7 is a sectional view showing the third embodiment of the present invention. The sensor unit 300 of the third embodiment has a measurement module 39 to store the atmosphere measuring means 19 such as the $CO_2$ concentration and the oxygen concentration and filter modules 40 to form the suction port and the exhaust port each having a filter 34, which are arranged apart. The measurement module 39 is communicated with each filter module 40 through a tube via joints. Besides, the measurement module 39 and the filter modules 40 are blocks formed of aluminum members, whose surfaces are alumite-treated.

The measurement module 39 has the inhalation passage 26 and the discharge passage 27 as well as the first and second embodiments. The pump 21 is air-tightly fixed on sides of these two through holes opposite to sides facing the incubation chamber 2 through a packing sheet 25. And the measurement module 39 has a sensor hole 31 orthogonal to the inhalation passage 26, in which the atmosphere measuring means 19 is inserted. In addition, the electric heater 36 and the thermocouple are provided to heat the measurement module 39 as well as the first and the second embodiments. The measurement module 39 has two tapered thread holes to attach the couples 41 at opening portions of the inhalation passage 26 and the discharge passage 27 opposite to the side where the pump 21 is arranged. The couples 41 are respectively inserted in the two thread holes. The measurement module 39 is fixed to the inside of the incubator 1 through a not-illustrated bracket. Further, the measurement module 39 is almost entirely covered with the heat insulator 14.

Each filter module 40 has a through hole 42 formed around the center. The thread hole 42 has a tapered thread hole to attach the couple 41 at an opening portion opposite to the side contacting with the wall of the incubation chamber 2. The couple 41 is inserted in the thread hole. The through hole 42 of the wall side of the incubation chamber 2 has a larger diameter than that of the thread hole attached the couple 41. The filter module 40 of the wall side of the incubation chamber 2 has a cavity having a somewhat larger diameter than that of the through hole 42 over the entire periphery. And the filter 34 formed by processing and sintering minute fibers made of steel materials of stainless 316 is screwed in the cavity through the presser plate 35 like the first embodiment. Although the used filter 34 is the same as the first and the second embodiments, for example, it can be formed from synthetic fibers such as polypropylene, polyester, or polyolefin. Besides, the filter module 40 also has the electric heater 36 and the thermocouple to handle the dew condensation according to the lowering of the atmosphere pressure after passing through the filter 34 as well as the measurement module 39, thereby preventing from the dew condensation of the internal space of the block formed by the filter 34 and the filter module 40.

The filter module 40 is fixed to the opening portion of the wall surface of the incubation chamber 2. The opening portion is formed in a shape of the filter module 40. A fixing method can be applied for a method by providing a tapped hole to the filter module 40 to be fixed from the inside of the incubation chamber 2 with screws, or a method by welding studs and nuts on the outside wall surface of the incubation chamber 2 to be fixed from the outside of the incubation chamber 2 with screws and nuts. Besides, the packing 23 is provided between the filter module 40 and the wall surface of the incubation chamber 2 to prevent the air inside the incubation chamber 2 from leaking to the outside and simultaneously to prevent the air from the outside from flowing into the sensor unit 300 and the incubation chamber 2.

In the sensor unit 300 of this embodiment, two filter modules 40 for inhalation and for discharge are provided on the wall surface of the incubation chamber 2, and each of the filter modules 40 is connected to the measurement module 39 through the coupling 41 and the tube 43 allowing air to pass therethrough. According to this structure, the air inside the incubation chamber 2 is inhaled into the sensor unit 300 through the filter module 40 connected to the inhalation passage 26 under the condition which the outside air is blocked, and then, the once-inhaled air is returned into the incubation chamber 2 through the filter module 40 connected to the discharge passage 27 under the condition which the outside air is blocked.

Besides, if the coupling 41 is made of metal such as stainless steel, the coupling 41 can withstand the dry heat sterilization for killing the unwanted bacteria by heating the incubation chamber 2. Further, the tube 43 can also withstand the dry heat sterilization by being made of metal, fluoric resin or silicon. Furthermore, the inside of the tube 43 can be prevented from being dew-condensed by putting an electric heater 36 shaped in a sheet and the heat insulator around the periphery of the tube 43. If the electric heater 36 is not necessary, only the heat insulator should be put around. With reference to the pump 21, explanation is omitted because it is the same as the first and the second embodiments.

According to the above-mentioned construction, like the first and the second embodiments, it is possible to prevent corrosion of the detecting elements of the sensor by the sterilization gas and the high humidity atmosphere. Therefore, it is possible to stably detect after culturing for a long time or sterilizing repeatedly. Besides, because this embodiment can also have each of the filter modules 40 at the predetermined position individually, it is possible to arrange the filter modules 40 of the inhalation side and the discharge side at most suitable positions respectively. Further, because the measurement module 39 having the pump 21 relatively weak to high temperature and the atmosphere measuring means 19 such as the $CO_2$ sensor and the oxygen sensor is located at the position apart from the incubation chamber 2, it is possible to carry out dry-heat sterilization for keeping the inside of the incubation chamber 2 in hot temperature atmosphere. Furthermore, if a plurality of filter modules 40 of the inhalation side are provided and the tube 43 from each filter module 40 is operated by a switching valve, it is possible to measure the atmosphere inside the incubation chamber 2 from the plurality of different positions sequentially. Therefore, it is possible to measure the inside atmosphere exactly.

Figure 8:
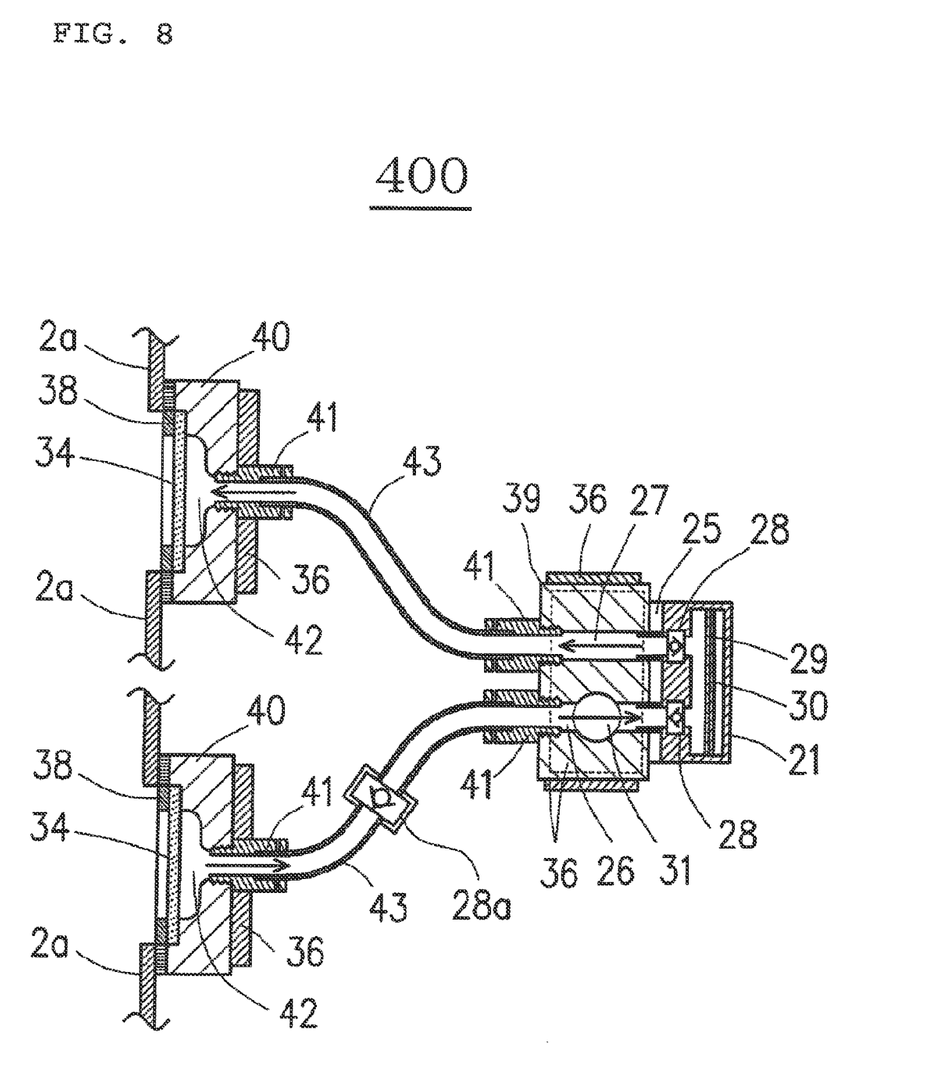
FIG. 8 is a sectional view showing the fourth embodiment of the sensor unit.

Further, like the first embodiment, the present embodiment can also provide with the check valve 28a between the atmosphere measuring means 19 of the measurement module 39 and the filter 23 to prevent invasion of the sterilization gas such as hydrogen peroxide gas in the measurement module 39 by diffusion like the first embodiment. FIG. 8 is a sectional view of the fourth embodiment having the check valve 28a. In the sensor unit 400 of the fourth embodiment, the check valve 28a is provided on the tube 43 connecting the measurement module 39 and the filter module 40 of the inhalation side. However, the check valve 28a and a relief valve can be provided anywhere between the atmosphere measuring means 19 and the filter 23 of the inhalation side because it is the object to protect the atmosphere measuring means 19 from the sterilization gas. In the fourth embodiment, it is possible to selectively control the inflow of gas into the measurement module 39 by using the difference between the pressure inhaled with the pump 21 and the pressure intruded by diffusion of the sterilization gas like the second embodiment.

Further, in this embodiment, it is possible to easily arrange the switching valve between the atmosphere measuring means 19 and the filter 23 of the inhalation side because the filter module 40 and the measurement module 39 are located away. The switching valve consists of members with the tolerance to the sterilization gas. If the switching valve is opened in culturing, the atmosphere inside the incubation chamber 2 can be inhaled and detected. And, if it is closed in sterilizing, the sterilization gas can be prevented from entering the measurement module 39. The switching valve can be operated by hand or by electricity. Furthermore, the switching valve can be provided on the passage of the discharge side as well as the inhalation side.

Although the present invention has been described along preferred embodiments, it is to be understood that the present invention is not limited to the specific embodiments thereof. It is understood that the present invention can be applied for isolators, automated cell culture equipment, incubators and various cytoscopy equipment etc. except the incubator 1, which can enough play the effect equal to these embodiments. It will be obvious to those skilled in the art that modifications, improvements and combinations may be made in the present invention without departing the spirit and scope thereof.

EXPLANATION OF REFERENCED NUMERALS

100 sensor unit (the first embodiment)
200 sensor unit (the second embodiment)
300 sensor unit (the third embodiment)
400 sensor unit (the fourth embodiment)
1 incubator
2 incubation chamber
2a incubation chamber wall
3 inner door
4 shelf
5a $CO_2$ supply pipe
5b $N_2$ gas supply pipe
6a $CO_2$ supply switching valve
6b $N_2$ gas supply switching valve
7 supply port
7a pipe
7b switching valve 8 suction port
8a pipe
8b switching valve
9 outer door
10 packing
11 outer case
12 packing
13 electric heater
14 heat insulator material
15 soaking board
16 inside panel
17 water tray
18 thermal sensor
19 atmosphere measuring means
20 air-flow generation means
21 pump
22 body module
23 filter
24 packing
25 sheet packing
26 inhalation passage
27 discharge passage
28 check valve
28a check valve
29 partition
30 bimorph trembler
31 sensor hole
32 detecting portion
33 O-ring
34 filter
35 presser plate
36 electric heater
37 duct
38 presser plate
39 measurement module
40 filter module
41 coupling
42 through hole
43 tube

The invention claimed is:

1. A sensor unit comprising:
a block having an interior space to be communicated with an incubation chamber,
an air-flow generation means for sucking atmosphere from the incubation chamber to the interior space of the block and through at least a portion of the air-flow generation means and subsequently directing atmosphere from the air-flow generation means into the interior space of the block and subsequently discharging the atmosphere into the incubation chamber;
an atmosphere measuring means for measuring the atmosphere sucked into the interior space;
at least one filter configured to be arranged between the incubation chamber and the interior space; and
a block heater for heating the atmosphere in the block when sucked through the at least one filter,
wherein the block has an inhalation passage for communicating the atmosphere sucked by the air-flow generation means, said inhalation passage provided as the interior space, and a discharge passage for returning the sucked atmosphere to the incubation chamber by the air-flow generation means, and
wherein the at least one filter having a first filter portion and a second filter portion, said first filter portion is arranged between the incubation chamber and the inhalation passage and said second filter portion is arranged between the incubation chamber and the discharge passage.

2. A sensor unit as claimed in claim 1, wherein the air-flow generation means is a pump having a suction port and an exhaust port, and
the inhalation passage and the discharge passage are connected to the suction port and the exhaust port of the pump, respectively.

3. A sensor unit as claimed in claim 2, wherein the atmosphere measuring means is located in the inhalation passage.

4. A sensor unit as claimed in claim 1, wherein the at least one filter is made of sintered metal.

5. A sensor unit as claimed in claim 3, wherein the heater heats atmosphere inside the inhalation passage.

6. A sensor unit as claimed in claim 3, further comprising a check valve having cracking pressure lower than pressure that the pump can suck, being provided between the at least one filter and the atmosphere measuring means, said at least one filter being provided to an inhalation passage side.

7. A sensor unit as claimed in claim 2, wherein the block is made of metal and has two through holes in parallel, said through holes passing through from one surface to another surface, one being the inhalation passage and another being the discharge passage, and the heater heats the block made of metal.

8. A constant-temperature device comprising:
an incubation chamber; and
a sensor unit comprising:
a block having an interior space to be communicated with an incubation chamber,
an air-flow generation means for sucking atmosphere from the incubation chamber to the interior space of the block and through at least a portion of the air-flow generation means and subsequently directing atmosphere from the air-flow generation means into the interior space of the block and subsequently discharging the atmosphere into the incubation chamber;
an atmosphere measuring means for measuring the atmosphere sucked into the interior space;
at least one filter configured to be arranged between the incubation chamber and the interior space; and
a block heater for heating the atmosphere in the block when sucked through the at least one filter,
wherein the block has an inhalation passage for communicating the atmosphere sucked by the air-flow generation means, said inhalation passage provided as the interior space, and a discharge passage for returning the sucked atmosphere to the incubation chamber by the air-flow generation means, and
wherein the at least one filter having a first filter portion and a second filter portion, said first filter portion is arranged between the incubation chamber and the inhalation passage and said second filter portion is arranged between the incubation chamber and the discharge passage.

9. The constant-temperature device as claimed in claim 8, wherein the air-flow generation means is a pump having a suction port and an exhaust port, and
the inhalation passage and the discharge passage are connected to the suction port and the exhaust port of the pump, respectively.

10. The constant-temperature device as claimed in claim 9, wherein the atmosphere measuring means is located in the inhalation passage.

11. The constant-temperature device as claimed in claim 8, wherein the at least one filter is made of sintered metal.

12. The constant-temperature device as claimed in claim 10, wherein the heater heats atmosphere inside the inhalation passage.

13. The constant-temperature device as claimed in claim 10, further comprising a check valve having cracking pressure lower than pressure that the pump can suck, being provided between the at least one filter and the atmosphere measuring means, said at least one filter being provided to an inhalation passage side.

14. The constant-temperature device as claimed in claim 9, wherein the block is made of metal and has two through holes in parallel, said through holes passing through from one surface to another surface, one being the inhalation passage and another being the discharge passage, and the heater heats the block made of metal.

15. A sensor unit as claimed in claim 1, wherein:
said first filter portion and said second filter portion are portions of a single filter.

16. A sensor unit as claimed in claim 1 wherein:
said first filter portion forms a first filter and said second filter portion forms a second filter.

\* \* \* \* \*